United States Patent [19]

Fukumoto et al.

[11] Patent Number: 4,760,196

[45] Date of Patent: Jul. 26, 1988

[54] METHOD FOR PREPARING AN ALDEHYDE OR ALCOHOL BY REDUCTION OF A CARBOXYLIC ACID

[75] Inventors: Takehiko Fukumoto; Akira Yamamoto, both of Niigata, Japan

[73] Assignee: Shin-Etsu Chemical Co., Ltd., Tokyo, Japan

[21] Appl. No.: 47,612

[22] Filed: May 8, 1987

[30] Foreign Application Priority Data

May 12, 1986 [JP] Japan ................................ 61-108274

[51] Int. Cl.$^4$ ............................................. C07C 45/54
[52] U.S. Cl. .................................... 568/484; 568/490; 568/864
[58] Field of Search ............... 568/484, 490, 485, 864, 568/886

[56] References Cited

U.S. PATENT DOCUMENTS 4,156,791   5/1979   Childs .................................. 568/864

OTHER PUBLICATIONS

Nystron, "J. Amer. Chem. Soc.", vol. 69, pp. 2548 (1947).
Brown et al., "J. Amer. Chem. Soc.", vol. 75, p. 6263 (1953).
Pettit et al., "J. Organic Chem.", vol. 27, p. 2127 (1962).

*Primary Examiner*—Werren B. Lone
*Attorney, Agent, or Firm*—Jules E. Goldberg

[57] ABSTRACT

The inventive method is particularly advantageous for the preparation of an unsaturated alcohol or aldehyde by the reduction of a corresponding unsaturated carboxylic acid since the unsaturated double bond in the starting acid is not hydrogenated by the reaction of reduction. The method comprises first reacting the starting acid with an alkyl chloroformate to form an intermediate compound by the dehydrochlorination and the intermediate compound is then reduced by using sodium borohydride as the reducing agent. The proportion of the aldehyde to alcohol in the product mixture can be controlled by modifying the amount of the reducing agent and/or the reaction time.

3 Claims, No Drawings

METHOD FOR PREPARING AN ALDEHYDE OR ALCOHOL BY REDUCTION OF A CARBOXYLIC ACID

BACKGROUND OF THE INVENTION

The present invention relates to a method for preparing an aldehyde or alcohol by the reduction of a carboxylic acid or, more particularly, to a method for preparing an aldehyde or alcohol by the reduction of a corresponding carboxylic acid using a metal borohydride as the reducing agent.

When an aldehyde or an alcohol compound is desired to be prepared by the reduction of a corresponding carboxylic acid, it is a usual practice that the carboxylic acid is reduced as a solution in diethyl ether or tetrahydrofuran using lithium aluminum hydride LiAlH$_4$ as the reducing agent. The applicability of this reducing method, however, is limited even by setting aside the problem of expensiveness of this reagent to probibit industrial application of the method. For example, reduction of an unsaturated carboxylic acid by this method is not always suitable for the preparation of the corresponding unsaturated aldehyde or alcohol since the reduction takes place not selectively at the carboxyl group alone but also the unsaturated linkage in the unsaturated carboxylic acid is also susceptible to reduction. When cinnamic acid is reduced in an ether solution by using lithium aluminum hydride as the reducing agent, for example, the reaction product is not the desired cinnamyl alcohol but dihydro-cinnamyl alcohol as is taught by R. F. Nystron, et al. in Journal of the American Chemical Society, volume 69, page 2548 (1947).

The unsaturated linkage in the unsaturated carboxylic acid may be protected from reduction by using a reducing agent system of lithium aluminum hydride combined with anhydrous aluminum chloride. For example, sorbic acid CH$_3$CH=CH—CH=CH—COOH can be reduced by this method into hexa-2,4-dienol CH$_3$CH=CH—CH=CH—CH$_2$OH. This method, however, is not practical due to the extremely low yield of the reaction product of, for example, only 20% in the above mentioned reduction of sorbic acid. Moreover, the reaction product in the reduction of a carboxylic acid using lithium aluminum hydride is always the corresponding alcohol while the corresponding aldehyde compound, which should have been formed at the intermediate stage, can hardly be obtained as the final product.

Sodium borohydride is less expensive as a reducing agent than lithium aluminum hydride and is used in various synthetic reactions. The reducing power of this reducing agent is, however, not strong enough to reduce a carboxylic acid into a corresponding aldehyde or alcohol. The reducing power of sodium borohydride can be strengthened by performing the reducing reaction in diglyme as the solvent by combining sodium boorhydride with anhydrous aluminum chloride as is taught by H. C. Brown et al. in Journal of the American Chemical Society, volume 75, page 6263 (1953) or by combining sodium borohydride with boron trifluoride BF$_3$ as is taught by G. R. Pettit, et al. in Journal of Organic Chemistry, volume 27, page 2127 (1962).

These improved methods for increasing the reducing power of sodium borohydride are still not quite satisfactory due to the use of a Lewis acid such as anhydrous aluminum chloride and boron trifluoride. Namely, the procedure of the reaction is usually troublesome and the reaction is sometimes accompanied by undesirable side reactions when the product is not sufficiently stable resulting in decrease in the yield of the desired product. The selectivity of the reducing reaction is also not without problems. In addition, the diglyme used as the solvent can be recovered with some difficulties and the waste material containing aluminum chloride may be responsible for very serious environmental pollution when the waste water is discharged to public waterway without appropriate treatment of sewage disposal.

Lithium aluminum hydride and sodium borohydride both belong to a class of typical complex compounds capable of reducing various kinds of organic compounds by releasing hydrogen in the form of hydride ions. The problems in these hydrides as an industrial reducing agent are the expensiveness of lithium aluminum hydride having a relatively high reducing power and the relatively low reducing power of the less expensive sodium borohydride necessitating combined use of an auxiliary reagent to cause complicacy of the process and low yield of the product. At any rate, each of these hydrides is not suitable as a reducing agent when a carboxylic acid should be reduced to the corresponding aldehyde and not to the alcohol.

SUMMARY OF THE INVENTION

An object of the present invention is therefore to provide a method for the preparation of an aldehyde or alcohol by reducing a carboxylic acid using a metal borohydride or, in particular, sodium borohydride as the reducing agent.

Another object of the invention is to provide a method for preparing an unsaturated aldehyde or alcohol by reducing a corresponding unsaturated carboxylic acid with a metal borohydride as the reducing agent without affecting the unsaturated linkage in the acid.

Thus, the method of the present invention for the preparation of an aldehyde of the general formula RCHO or alcohol of the general formula RCH$_2$OH, in which R is a monovalent hydrocarbon group having 1 to 20 carbon atoms selected from the class consisting of alkyl, alkenyl, alkynyl and aryl groups, by reducing a carboxylic acid comprises the steps of:

(a) reacting a carboxylic acid represented by the general formula $$R-CO-OH, \qquad (I)$$

in which R has the same meaning as defined above, and a chloroformate ester represented by the general formula $$ClCO-OR^1, \qquad (II)$$

in which R$^1$ is a monovalent hydrocarbon group having 1 to 20 carbon atoms selected from the class consisting of alkyl, alkenyl, alkynyl and aryl groups or, in particular, alkyl groups, in the presence of an acid acceptor to form an intermediate compound represented by the general formula $$R-CO-O-CO-OR^1, \qquad (III)$$

in which R and R$^1$ each have the same meaning as defined above; and (b) reducing the intermediate compound with an alkali metal borohydride, such as sodium borohydride NaBH$_4$ and lithium borohydride LiBH$_4$ or, preferably, sodium borohydride, as the reducing agent into the aldehyde of the formula RCHO or alcohol of the formula $RCH_2OH$.

DETAILED DESCRIPTION OF THE PREFERRED EMBODIMENTS

As is described in the above given summary of the invention, the starting carboxylic acid is reduced by the metal borohydride not in the form of the free acid but in the form of a very specific intermediate compound something like an acid anhydride which is formed by the dehydrochlorination reaction between the starting carboxylic acid and a chloroformate ester. This method of reduction is very advantageous because, if not to mention the inexpensiveness of the reducing agent, the reducing reaction can be controlled to give an aldehyde compound which is intermediate in the course of the full reduction of the acid into an alcohol and, when the starting carboxylic acid is an unsaturated acid, the unsaturated linkage is not affected as a result of the selective reduction at the carboxyl group of the acid alone.

The starting carboxylic acid to be reduced by the inventive method is represented by the above given general formula (I), in which the group denoted by R is a monovalent hydrocarbon group having 1 to 20 carbon atoms and any of the carboxylic acid in conformity with the general formula and definition of R can be used as the starting material according to desire although the inventive method is most advantageously applied to the preparation of an unsaturated aldehyde or alcohol starting from an unsaturated acid. The chloroformate ester to be reacted with the starting carboxylic acid is represented by the general formula (II) although alkyl chloroformates or, in particular, methyl and ethyl chloroformates are preferred in respect of the inexpensiveness.

The reaction of the starting carboxylic acid and the chloroformate ester is performed in an organic solvent at a temperature in the range from $-20°$ C. to $+20°$ C. in the presence of an acid acceptor which should be an organic base compound such as tertiary amines, e.g., triethyl amine and pyridine. The organic solvent suitable as the reaction medium is exemplified by dialkyl ethers, e.g., diethyl ether, cyclic ethers, e.g., tetrahydrofuran, 1,2-dimethoxy ethane, i.e. diglyme, and the like and should desirably be completely dehydrated prior to use. The intermediate compound is readily formed by adding the chloroformate ester into a solution of the starting carboxylic acid kept at the above mentioned temperature by the dehydrochlorination reaction between the reactant. The hydrogen chloride formed by the reaction is caught by the acid acceptor to form precipitates such as triethyl amine hydrochloride. Although the reaction mixture containing the precipitates of the salt can be used as such in the next step of reduction, it is preferable that the precipitates should be removed by filtration and the filtrate containing the intermediate compound is used in the step of reduction in order to improve the yield of the product. The intermediate compound of the general formula (III) is generally an unstable compound so that the reaction mixture containing the interme-iate compound should be processed as quickly as possible in order to minimize the possible loss thereof by decomposition.

The reaction of reduction is performed by adding the above obtained solution containing the intermediate compound dropwise into a suspension of the metal borohydride in an organic solvent. The reaction temperature should be in the range from $-50°$ C. to $+30°$ C. When an aldehyde compound is the desired product, the temperature should preferably be in the range from $-50°$ C. to $0°$ C. so that the yield of the aldehyde compound can be increased relative to the alcohol compound. The solvent used in this step may be the same one as in the reaction of the starting carboxylic acid and the chloroformate ester including dialkyl ethers, e.g. diethyl ether, cyclic ethers, e.g., tetrahydrofuran, 1,2-dimethoxy ethane, i.e. diglyme, and the like. It is not necessary that the solvent used in the reaction of reduction is anhydrous and a mixture of water and an organic solvent can be used without particularly disadvantageous effect provided that the reactants are soluble in the medium. Tetrahydrofuran is one of the preferred organic solvents which can be used in both steps for the preparation of the intermediate compound and for the reduction of the same.

The amount of the metal borohydride used in the reduction depends on the desired reaction product which may be an aldehyde compound or an alcohol compound. When the desired product is an aldehyde compound, the metal borohydride should be used in an amount in the range from 1.0 to 1.5 moles per mole of the starting carboxylic acid and the reaction should be continued for 2 to 6 hours although the reaction product is always a mixture of the aldehyde compound and the alcohol compound. When an alcohol compound is the desired product, on the other hand, the amount of the reducing agent should be increased to 1.5 to 2.5 moles per mole of the starting carboxylic acid and the reaction should be continued for 1 to 5 hours. The yield of the reaction products is usually lower under the reaction conditions where the major product is the aldehyde compound than under the reaction conditions where the major product is the alcohol compound. When the amount of the metal borohydride is increased to 3 moles per mole of the starting carboxylic acid, the reaction of reduction would be complete so that the resultant reaction product can be substantially free from the aldehyde compound as the intermediate reduction product. After completion of the reaction of reduction, the reaction mixture was admixed with hydrochloric acid of a concentration of, for example, 10 to 20% followed by phase separation and the desired product of the alcohol or aldehyde compound can readily be isolated from the organic phase by a conventional procedure.

When the inventive method was applied to the reduction of 1 mole of sorbic acid $CH_3CH=CHCH=CHCOOH$ which is first reacted with ethyl chloroformate $ClCOOC_2H_5$ to give an intermediate compound followed by reduction of the same with 2.0 moles of sodium borohydride in tetrahydrofuran at 10° to 15° C., the resultant reaction mixture contained 9% by weight of sorbic aldehyde $CH_3CH=CHCH=CHCHO$ and 58% by weight of sorbyl alcohol $CH_3CH=CHCH=CH_2OH$. When 1 mole of cinnamic acid $C_6H_5CH=CHCOOH$ was first reacted with methyl chloroformate $ClCOOCH_3$ to give an intermediate compound followed by reduction of the same with 1.3 moles of sodium borohydride in tetrahydrofuran at $-10°$ to 5° C., the resultant reaction mixture contained 25% by weight of cinnamic aldehyde $C_6H_5CH=CHCHO$ and 20% by weight of cinnamyl alcohol $C_6H_5CH=CHCH_2OH$.

In the following, examples and comparative examples are given to illustrate the method of the invention in more detail but not to limit the scope of the invention in any way.

EXAMPLE 1

Into a solution prepared by dissolving 28 g (0.25 mole) of sorbic acid in 100 ml of tetrahydrofuran with admixture of 25 g of triethyl amine kept at 0° to 10° C. were added dropwise 27 g of ethyl chloroformate over a period of 30 minutes with agitation. After completion of the dropwise addition of ethyl chloroformate, the mixture was further agitated for additional 30 minutes at 10° C. and then quickly filtered to remove the precipitates of triethyl amine hydrochloride. Thereafter, a suspension of 19 g (0.5 mole) of sodium borohydride in 100 ml of tetrahydrofuran was added dropwise into the above obtained filtrate solution kept at 10° to 15° C. under an atmosphere of nitrogen. After completion of the dropwise addition of the suspension, the reaction mixture kept at 20° C. was further agitated for additional 30 hours and 100 ml of a 10% hydrochloric acid were added thereto followed by phase separation. The organic solution taken by phase separation was subjected to evaporation in a rotary evaporator to remove tetrahydrofuran and then distilled under reduced pressure to give 16.4 g of a fraction boiling at 80° to 86° C. under a pressure of 10 mmHg as a product. Gas chromatographic analysis of this product indicated that the product was a 14:86 by weight mixture of 2,4-hexadien-1-al, i.e. sorbic aldehyde, and 2,4-hexadien-1-ol, i.e. sorbyl alcohol. The yield was 67% of the theoretical value.

EXAMPLE 2

The experimental procedure was substantially the same as in Example 1 excepting increase of the amount of sodium borohydride to 28.5 g (0.75 mole). The yield of the fraction boiling at 85° to 86° C. under a pressure of 10 mmHg was 16.7 g and the gas chromatographic analysis indicated that this product was 2,4-hexadien-1-ol substantially free from the aldehyde compound. The yield was 68% of the theoretical value.

COMPARATIVE EXAMPLE 1

Into a solution of 12 g (0.31 mole) of lithium aluminum hydride in 100 ml of anhydrous tetrahydrofuran kept at 0° to 10° C. were added gradually 13 g (0.1 mole) of anhydrous aluminum chloride and the mixture was agitated for 30 minutes at 10° C. In the next place, a solution of 28 g (0.25 mole) of sorbic acid dissolved in 100 ml of anhydrous tetrahydrofuran was added dropwise to the reaction mixture kept at 0° to 20° C. over a period of 1 hour. After completion of the dropwise addition of the solution, the reaction mixture was admixed with 100 ml of a 10% hydrochloric acid followed by phase separation. The organic solution taken by phase separation was subjected to evaporation of tetrahydrofuran in a rotary evaporator and then distilled under reduced pressure to give 4.9 g of 2,4-hexadien-1-ol in a yield of 20% of the theoretical value.

COMPARATIVE EXAMPLE 2

Into a solution of 12 g (0.3 mole) of sodium borohydride in 100 ml of diglyme were added 13 g (0.1 mole) of anhydrous aluminum chloride gradually at 0° to 10° C. and the mixture was agitated for 30 minutes at 10° C. Thereafter, a solution of 28 g (0.25 mole) of sorbic acid in 100 ml of anhydrous diglyme was added dropwise to the mixture at 0° to 20° C. over a period of 1 hour. After completion of the dropwise addition of the solution, the mixture was admixed with 100 ml of a 10% hydrochloric acid followed by phase separation and the organic solution taken by phase separation was distilled under reduced pressure to give 4.0 g of a fraction boiling at 79° to 81° C. under a pressure of 15 mmHg. Gas chromatographic analysis of this product indicated that the product was composed of 5.1% by weight of 2,4-hexadien-1-ol and 94.9% by weight of n-hexyl alcohol. The yields of these products were 5.1% and 19%, respectively, of the theoretical values relative to the starting amount of the sorbic acid.

EXAMPLE 3

The experimental conditions in each of the four synthetic experiments were approximately the same as in Example 1 except that the starting carboxylic acid was cinnamic acid in an amount of 37 g (0.25 mole) instead of 28 g (0.25 mole) of sorbic acid and the reaction temperature and the amount of sodium borohydride were varied as shown in the table below, which also includes the yield of the products relative to the theoretical value and the weight ratio of cinnamic aldehyde to the cinnamyl alcohol in each of the experiments.

| Reaction temperature, °C. | Moles of NaBH$_4$ per mole of acid | Yield, % | Ratio of aldehyde to alcohol |
|---|---|---|---|
| 0–20 | 3.0 | 75 | 0:100 |
| 10–15 | 2.0 | 69 | 12:88 |
| 0–10 | 1.5 | 55 | 31:69 |
| 10–5 | 1.2 | 45 | 55:45 |

COMPARATIVE EXAMPLE 3

Into a solution of 12 g (0.31 mole) of lithium aluminum hydride in 100 ml of anhydrous diethyl ether was added dropwise a solution prepared by dissolving 37 g (0.25 mole) of cinnamic acid in 100 ml of anhydrous diethyl ether at a temperature of 0° to 20° C. After completion of the dropwise addition of the solution, the mixture was further agitated for additional 30 minutes at 20° C. and then admixed with 100 ml of a 10% hydrochloric acid followed by phase separation. The organic solution taken by phase separation was subjected to evaporation of the ether and then distilled under reduced pressure to give 11 g of dihydrocinnamyl alcohol, which yield was 31% of the theoretical value, but neither cinnamyl alcohol nor cinnamic aldehyde could be obtained.

What is claimed is:

1. A method for the preparation of an aldehyde of the general formula RCHO or an alcohol of the general formula RCH$_2$OH, in which R is a monovalent hydrocarbon group having 1 to 20 carbon atoms selected from the class consisting of alkyl, alkenyl, alkynyl and aryl groups, from a carboxylic acid represented by the general formula RCOOH, in which R has the same meaning as defined above, which comprises the steps of:
   (a) reacting at a temperature in the range from −20° C. to +20° C., a carboxylic acid represented by the general formula

R—CO—OH, in which R has the same meaning as defined above, and a chloroformate ester represented by the general formula ClCO—OR¹, in which R¹ is a monovalent hydrocarbon group having 1 to 20 carbon atoms selected from the class consisting of alkly, alkenyl, alkynyl and aryl groups, in the presence of an acid acceptor selected from the group consisting of organic base compounds to form an intermediate compound represented by the general formula

R—CO—O—CO—OR¹, in which R and R¹ each have the same meaning as defined above; and (b) reducing the intermediate compound with sodium borohydride as the reducing agent at a temperature from −50° C. to +30° C. into the aldehyde of the formula RCHO or alcohol of the formula RCH₂OH.

2. The method as claimed in claim 1 wherein the alkyl chloroformate is methyl or ethyl chloroformate.

3. A method for the preparation of an aldehyde of the general formula RCHO or an alcohol of the general formula RCH₂OH, in which R is a monovalent hydrocarbon group having 1 to 20 carbon atoms and containing at least one ethylenically unsaturated linkage, from a carboxylic acid represented by the general formula RCOOH, in which R has the same meaning as defined above, which comprises the steps of:

(a) reacting at a temperature in the range from −20° C. to +20° C., a carboxylic acid represented by the general formula

R—CO—OH, in which R has the same meaning as defined above, and an alkyl chloroformate represented by the general formula ClCO—OR¹, in which R¹ is a monovalent hydrocarbon group having 1 to 20 carbon atoms selected from the class consisting of alkyl, alkenyl, alkynyl and aryl groups, in the presence of an acid acceptor selected from the group consisting of organic base compounds to form an intermediate compound represented by the general formula

R—CO—O—CO—OR¹, in which R and R¹ each have the same meaning as defined above; and (b) reducing the intermediate compound with sodium borohydride as the reducing agent at a temperature from −50° C. to +30° C. into the aldehyde of the formula RCHO or alcohol of the formula RCH₂OH.

* * * * *